US012611533B2

(12) United States Patent
Natesan et al.

(10) Patent No.: US 12,611,533 B2
(45) Date of Patent: Apr. 28, 2026

(54) ANNULAR VALVE SECUREMENT WITHIN A CATHETER ASSEMBLY

(71) Applicant: Becton, Dickinson and Company, Franklin Lakes, NJ (US)

(72) Inventors: Mohankumar Natesan, Singapore (SG); Kiat Jin Cheng, Singapore (SG); Say Kiong Toh, Singapore (SG); Jithendra Kumar Sathyanarayana Naidu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 747 days.

(21) Appl. No.: 17/731,082

(22) Filed: Apr. 27, 2022

(65) Prior Publication Data

US 2022/0355093 A1 Nov. 10, 2022

Related U.S. Application Data

(60) Provisional application No. 63/186,668, filed on May 10, 2021.

(51) Int. Cl.
*A61M 39/22* (2006.01)
*A61M 25/06* (2006.01)
*A61M 39/10* (2006.01)

(52) U.S. Cl.
CPC .......... *A61M 39/22* (2013.01); *A61M 25/065* (2013.01); *A61M 39/10* (2013.01); *A61M 2039/1077* (2013.01)

(58) Field of Classification Search
CPC .......... A61M 25/0606; A61M 25/0693; A61M 39/24; A61M 2039/242; A61M 2039/244;
(Continued)

(56) References Cited

U.S. PATENT DOCUMENTS 3,416,567 A * 12/1968 Olle ...................... F16K 11/027
137/853
5,098,405 A 3/1992 Peterson
(Continued)

FOREIGN PATENT DOCUMENTS

AU 2012318631 4/2014
CN 206183780 U * 5/2017 ........... A61B 5/0002
(Continued)

OTHER PUBLICATIONS

CN_206183780_U_I_MT, machine translation of CN_206183780_U (Year: 2017).*

*Primary Examiner* — Wesley G Harris
*Assistant Examiner* — Charles W Nichols
(74) *Attorney, Agent, or Firm* — Kirton McConkie; Whitney Blair; Kevin Stinger

(57) ABSTRACT

A catheter system may include a catheter assembly. The catheter assembly may include the catheter adapter, which may include a distal end, a proximal end, an inner surface forming a lumen, the lumen extending through the distal end and the proximal end, and a side port disposed between the distal end and the proximal end. The catheter assembly may include an annular valve, which may be disposed within the lumen and aligned with the side port. The annular valve may seal a fluid pathway from the side port to the lumen. The catheter assembly may include a retainer ring or a bump disposed proximal and/or proximate the annular valve within the lumen. The catheter assembly may include a catheter extending distally from the distal end of the catheter adapter.

14 Claims, 11 Drawing Sheets

(58) Field of Classification Search
CPC ...... A61M 25/0097; A61M 2039/2433; A61M 2039/2493; A61M 39/10; A61M 39/22; A61M 2039/1077; F16K 15/142; F16K 15/144; F16K 15/145
See application file for complete search history.

(56) References Cited

U.S. PATENT DOCUMENTS

| | | | |
|---|---|---|---|
| 8,308,691 B2 * | 11/2012 | Woehr ............. | A61B 5/150213 |
| | | | 604/167.03 |
| 8,622,972 B2 * | 1/2014 | Nystrom ........... | A61M 39/0606 |
| | | | 604/167.03 |
| 9,750,925 B2 * | 9/2017 | Ma ........................ | A61M 39/06 |
| 2009/0036836 A1 | 2/2009 | Nystrom et al. | |
| 2011/0046570 A1 * | 2/2011 | Stout ................. | A61M 39/0693 |
| | | | 604/246 |
| 2014/0364809 A1 | 12/2014 | Isaacson | |
| 2017/0348518 A1 | 12/2017 | Ma | |
| 2020/0188634 A1 * | 6/2020 | Woehr ............. | A61M 25/0097 |

FOREIGN PATENT DOCUMENTS

| | | | | |
|---|---|---|---|---|
| DE | 202007006190 | 9/2007 | | |
| EP | 1197242 | 4/2002 | | |
| EP | 3003450 | 4/2016 | | |
| WO | WO-2016142410 A1 * | 9/2016 | ........ | A61M 25/0097 |
| WO | 2018217781 | 11/2018 | | |
| WO | 2020242878 | 12/2020 | | |

* cited by examiner

ANNULAR VALVE SECUREMENT WITHIN A CATHETER ASSEMBLY

RELATED APPLICATIONS

This application claims the benefit of U.S. Provisional Patent Application No. 63/186,668, filed on May 10, 2021, entitled ANNULAR VALVE SECUREMENT WITHIN A CATHETER ASSEMBLY, which is incorporated herein in its entirety.

BACKGROUND

Catheters are commonly used for a variety of infusion therapies. Catheters may be used for infusing normal saline solution, various medicaments, total parenteral nutrition, or other fluids into a patient. Catheters may also be used to withdraw blood from the patient for diagnostic or other purposes.

A common type of catheter is a peripheral intravenous catheter ("PIVC") that is "over-the-needle." As its name implies, the PIVC that is over-the-needle may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and introducer needle are generally inserted at a shallow angle through the skin into the vasculature of the patient.

In order to verify proper placement of the introducer needle and/or the PIVC in the blood vessel, a clinician generally confirms that there is "flashback" of blood in a flashback chamber of the catheter assembly. Once placement of the needle has been confirmed, the clinician may remove the introducer needle, leaving the PIVC in place for future fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices, systems, and methods. In particular, the present disclosure relates annular valve securement within a catheter assembly. In some embodiments, a catheter system may include the catheter assembly. In some embodiments, the catheter assembly may include the catheter adapter, which may include a distal end, a proximal end, an inner surface forming a lumen, the lumen extending through the distal end and the proximal end, and a side port disposed between the distal end and the proximal end.

In some embodiments, the catheter assembly may include an annular valve, which may be disposed within the lumen and aligned with the side port. In some embodiments, the annular valve may seal a fluid pathway from the side port to the lumen. In some embodiments, the catheter assembly may include a retainer ring or a bump disposed proximal and/or proximate the annular valve within the lumen. In some embodiments, the catheter assembly may include a catheter extending distally from the distal end of the catheter adapter.

In some embodiments, the inner surface of the catheter adapter may include an undercut. In some embodiments, the retainer ring may be disposed within the undercut. In some embodiments, the undercut may correspond to a proximal undercut, and the inner surface of the catheter adapter may further include a distal undercut. In some embodiments, the annular valve may be disposed between the proximal undercut and the distal undercut.

In some embodiments, the annular valve may include silicon. In some embodiments, the annular valve may be cylindrical. In some embodiments, the retainer ring may be formed by molding. In some embodiments, the retainer ring may be plastic.

In some embodiments, the catheter system may include a needle assembly. In some embodiments, the needle assembly may include a needle hub and an introducer needle extending distally from the needle hub and through the retainer ring, the annular valve, and the catheter. In some embodiments, the side port may extend from a top of the catheter adapter. In some embodiments, the side port may be configured to receive a syringe. In some embodiments, the retainer ring or the bump are configured to reduce proximal movement of the annular valve in response to fluid infusion through the side port that opens the annular valve.

In some embodiments, a method of flushing the catheter assembly may include coupling an infusion device to the side port of the catheter adapter of the catheter assembly. In some embodiments, the method may include activating the infusion device. In some embodiments, in response to activating the infusion device, the annular valve may be opened to allow fluid to flow from the side port into the lumen. In some embodiments, in response to activating the infusion device, a proximal end of the annular valve may be forced against the retainer ring and the retainer ring may remain in place. In some embodiments, in response to activating the infusion device, a proximal end of the annular valve may be forced against the bump.

In some embodiments, the infusion device may include a syringe. In some embodiments, activating the infusion device may include depressing a plunger of the syringe. In some embodiments, the method may include uncoupling and removing the needle assembly from the catheter adapter. In some embodiments, the infusion device may be activated after the needle assembly is uncoupled and removed from the catheter adapter.

In some embodiments, the inner surface of the catheter adapter may include a stepped surface. In some embodiments, the stepped surface may include a distal surface, a proximal surface, and a transition surface disposed between the distal surface and the proximal surface. In some embodiments, the annular valve disposed within the lumen may seal the fluid pathway from the side port to the lumen. In some embodiments, the annular valve may contact the distal surface. In some embodiments, the catheter assembly may include a cavity disposed between an outer surface of the annular valve and the proximal surface. In some embodiments, the transition surface may form a distal end of the cavity.

In some embodiments, the transition surface may be disposed between the distal end of the annular valve and the proximal end of the annular valve. In some embodiments, the annular valve may contact the distal surface and a portion of the proximal surface. In some embodiments, the annular valve may contact the portion of the proximal surface to form a proximal end of the cavity. In some embodiments, a depth of the cavity may decrease in a proximal direction.

In some embodiments, the transition surface and the distal surface may meet at a sharp edge. In some embodiments, the stepped surface and the cavity may be semi-annular. In some embodiments, in response to infusion through the side port, the annular valve may decrease a size of the cavity. In some embodiments, the catheter assembly may include radial vertical ribs extending distally from the transition surface. In some embodiments, the proximal surface may include sand blasting or chemical etching.

In some embodiments, the stepped surface may correspond to a first stepped surface. In some embodiments, the inner surface of the catheter adapter may include a second stepped surface proximal to the first stepped surface. In some embodiments, the catheter assembly may include another cavity disposed between an outer surface of the annular valve. In some embodiments, another transition surface of the second stepped surface may form a distal end of the other cavity.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figures 1, 2A:
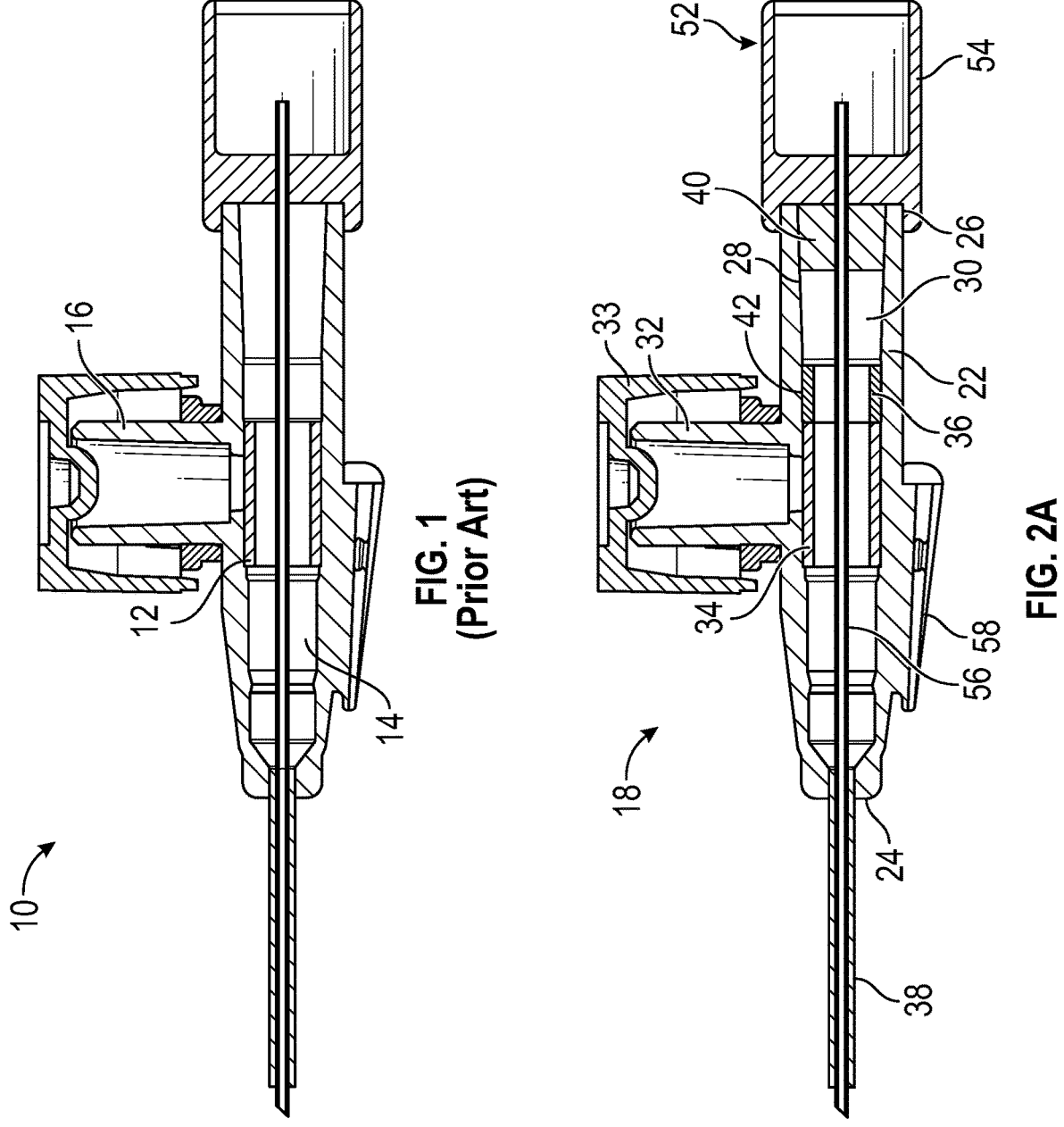
FIG. 1 is a cross-sectional view of a prior art catheter system.
FIG. 2A is a cross-sectional view of a catheter system, illustrating an example retainer ring, according to some embodiments.

Referring now to FIG. 1, a prior art catheter system 10 is illustrated. The prior art catheter system includes an annular valve 12 disposed in a catheter adapter lumen 14. The annular valve 12 is often moved proximally in response to fluid infusion through a side port 16 of the prior art catheter system 10. Proximal movement of the annular valve 12 may prevent the annular valve 12 from sealing the side port 16, and thus may result in leakage from the catheter adapter lumen 14 through the side port 16 following fluid infusion.

Figure 2B:
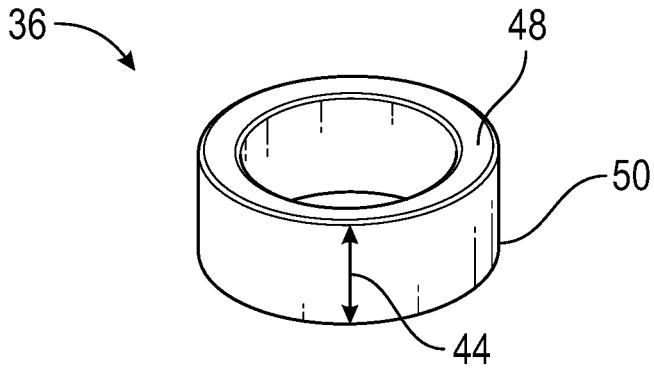
FIG. 2B is an upper perspective view of the retainer ring, according to some embodiments.
Figure 2C:
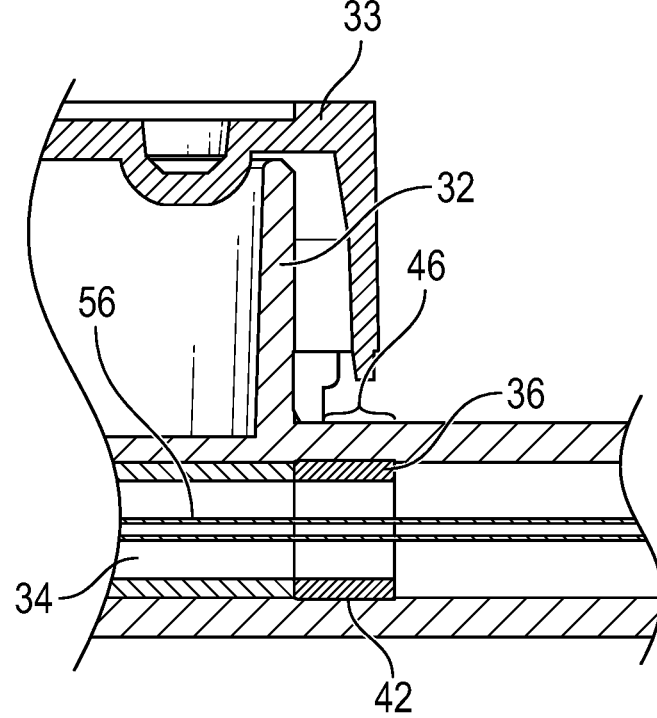
FIG. 2C is an enlarged cross-sectional view of a portion of the catheter system of FIG. 2A, according to some embodiments.

Referring now to FIGS. 2A-2C, a catheter system 18 is illustrated, according to some embodiments. In some embodiments, the catheter system 18 may include a catheter assembly 20. In some embodiments, the catheter assembly 20 may include a catheter adapter 22, which may include a distal end 24, a proximal end 26, an inner surface 28 forming a lumen 30. In some embodiments, the catheter assembly 20 may include the lumen 30 extending through the distal end 24 and the proximal end 26. In some embodiments, the catheter assembly 20 may include a side port 32 disposed between the distal end 24 and the proximal end 26. In some embodiments, the catheter assembly 20 may include a cap 33 removably coupled to the side port 32.

In some embodiments, the catheter assembly 20 may include an annular valve 34, which may be disposed within the lumen 30 and aligned with the side port 32. In some embodiments, the annular valve 34 may seal a fluid pathway from the side port 32 to the lumen 30. In some embodiments, the annular valve 34 may include silicon or another suitable material that allows an edge of the annular valve 34 to depress and open the fluid pathway from the side port 32 to the lumen 30 in response to fluid infusion through the side port 32. In some embodiments, the annular valve 34 may be cylindrical.

In some embodiments, the catheter assembly 20 may include a retainer ring 36 disposed proximal and/or proximate the annular valve 34 within the lumen 30. In some embodiments, the retainer ring 36 may be contacting the annular valve 34. In some embodiments, the catheter assembly 20 may include a catheter 38 extending distally from the distal end 24 of the catheter adapter 22. In some embodiments, the catheter 38 may include a peripheral intravenous catheter (PIVC), a midline catheter, a peripherally-inserted central catheter, or another suitable type of catheter.

In some embodiments, the catheter assembly 20 may include a septum 40, which may be disposed proximal to the retainer ring 36 and the annular valve 34. In some embodiments, the septum 40 may include silicon or another suitable material.

In some embodiments, the inner surface 28 of the catheter adapter 22 may include an undercut 42, which may be annular. In some embodiments, the retainer ring 36 may be disposed within the undercut 42. In some embodiments, a width 44 of the retainer ring 36 may be approximately equal to a length 46 of the undercut 42 such that a distal edge 48 of the retainer ring 36 and a proximal edge 50 of the retainer ring 36 may abut edges of the undercut 42. In some embodiments, the distal edge 48 and the proximal edge 50 may be annular. In some embodiments, the retainer ring 36 may fit snugly within the undercut 42. In some embodiments, an outer diameter may be slightly larger than a diameter of the undercut 42 such that the retainer ring 36 snaps into the undercut 42.

In some embodiments, the retainer ring 36 may be plastic, metal, or another suitable material. In some embodiments, the retainer ring 36 may be rigid or semi-rigid. In some embodiments, a durometer of the retainer ring 36 may be greater than a durometer of the annular valve 12. In some embodiments, the retainer ring 36 may be formed by molding. In further detail, in some embodiments, the retainer ring 36 may be formed by shaping a liquid or malleable raw material by using a fixed frame, such as a mold or a matrix. In some embodiments, the mold may include a hollow cavity receptacle into which the liquid or malleable raw material may be poured. In some embodiments, the liquid or malleable raw material may include plastic, metal, or another suitable material. As the liquid or malleable raw material hardens inside the mold, forming the retainer ring 36.

In some embodiments, the catheter system 18 may include a needle assembly 52. In some embodiments, the needle assembly 52 may include a needle hub 54 and an introducer needle 56 extending distally from the needle hub 54 and through the retainer ring 36, the annular valve 34, and the catheter 38. In some embodiments, the introducer needle 56 may include a sharp distal tip, which may facilitate placement of the catheter 38 within vasculature of a patient.

In some embodiments, the side port 32 may extend from a top of the catheter adapter 22 or a portion of the catheter adapter 22 opposite skin of the patient, which may be placed below the catheter adapter 22 and/or beneath one or more wings 58 extending outwardly from the catheter adapter 22.

Figure 2D:
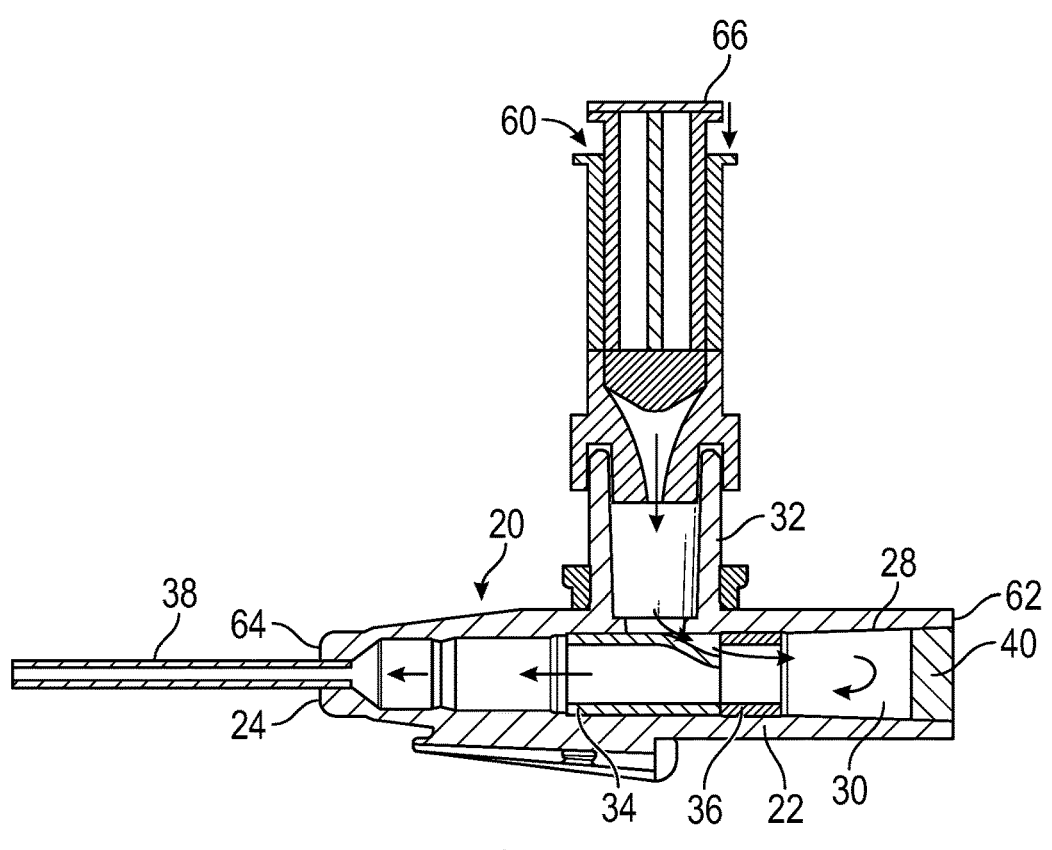
FIG. 2D is a cross-sectional view of the catheter system of FIG. 2A, illustrating an example infusion device coupled to an example side port and activated, according to some embodiments.

Referring now to FIG. 2D, in some embodiments, the side port 32 may be configured to receive an infusion device 60, which may include a syringe or another suitable infusion device configured to infuse fluid from the side port 32 into the lumen 30. In some embodiments, the retainer ring 36 is configured keep the annular valve 34 in a same or similar position in response to fluid infusion through the side port 32 that opens the annular valve 34. In further detail, in some embodiments, the retainer ring 36 may be configured to reduce proximal movement of the annular valve 34 in response to fluid infusion through the side port 32 that opens the annular valve 34. In some embodiments, in response to fluid infusion through the side port 32 that opens the annular valve 34, a proximal end 62 of the annular valve 34 may not move in a proximal direction and/or a distal direction. Thus, in some embodiments, the retainer ring 36 may prevent fluid, such as blood and/or another fluid, from leaking through the annular valve 34 and out the side port 32.

In some embodiments, the infusion device 60 may be activated in order to flush the catheter system 18 or inject a bolus. In some embodiments, a method of flushing the catheter assembly 20 may include coupling the infusion device 60 to the side port 32 of the catheter adapter 22 of the catheter assembly 20. In some embodiments, the side port 32 may include a luer, such as, for example, a female luer, which may be configured to couple to a corresponding luer of the infusion device 60.

In some embodiments, the method may include activating the infusion device 60. In some embodiments, in response to activating the infusion device 60, the annular valve 34 may be opened to allow fluid to flow from the side port 32 into the lumen 30. In some embodiments, in response to activating the infusion device 60, the proximal end 62 of the annular valve 34 opposite a distal end 64 of the annular valve 34 may be forced against the retainer ring 36 and the retainer ring 36 may remain in place. In these and other embodiments, the proximal end 62 of the annular valve 34 may not move in a proximal direction and/or a distal direction but may stay in place.

In some embodiments, the infusion device 60 may include the syringe, as illustrated, for example, in FIG. 2D. In some embodiments, activating the infusion device 60 may include depressing a plunger 66 of the syringe or otherwise causing fluid to be expelled from the infusion device into the catheter assembly 20. In some embodiments, the method may include uncoupling and removing the needle assembly 52 from the catheter adapter 22, as illustrated, for example, in FIG. 2D. In some embodiments, the infusion device 60 may be activated after the needle assembly 52 is uncoupled and removed from the catheter adapter 22.

Figure 2E:
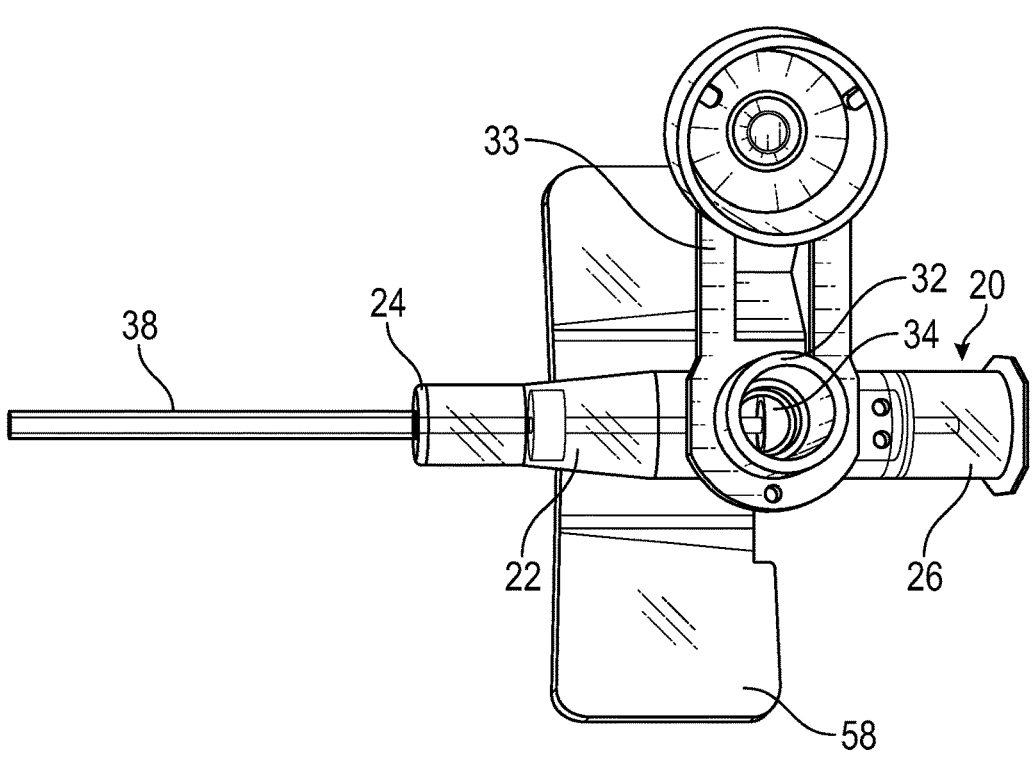
FIG. 2E is a top view of the catheter system of FIG. 2A following infusion through the side port, according to some embodiments.

Referring now to FIG. 2E, the catheter assembly 20 is illustrated with the cap 33 open after fluid infusion through the side port 32. As illustrated, the annular valve 34 is still in place and sealing the side port 32 after the fluid infusion.

Referring now to FIGS. 3A-3D, in some embodiments, a catheter assembly 68 is illustrated, according to some embodiments. In some embodiments, the catheter assembly 68 may be similar or identical to the catheter assembly 20 described with respect to FIG. 2 in terms of one or more features and/or operation. In some embodiments, the inner surface 28 of the catheter adapter 22 may include a stepped surface 70. In some embodiments, the stepped surface 70 may include a proximal surface 72, a distal surface 74, and a transition surface 76 disposed between the proximal surface 72 and the distal surface 74. In some embodiments, the annular valve 34 disposed within the lumen 30 may seal the fluid pathway from the side port 16 to the lumen 30, as illustrated, for example, in FIGS. 3B.

In some embodiments, the annular valve 34 may contact or rest on the distal surface 74. In some embodiments, the catheter assembly 20 may include a cavity 78 disposed between an outer surface 80 of the annular valve 12 and the proximal surface 72. In some embodiments, the outer surface of the annular valve 12 may be generally cylindrical. In some embodiments, the transition surface 76 may form a distal end of the cavity 78.

In some embodiments, the transition surface 76 may be disposed between the distal end 64 of the annular valve 12 and the proximal end 62 of the annular valve 34. In some embodiments, the annular valve 34 may contact the distal surface 74 and a portion 80 of the proximal surface 72, which may be spaced apart from the transition surface 76. In some embodiments, the annular valve 34 may contact the proximal surface 72 to form a proximal end of the cavity 78. In some embodiments, a depth of the cavity 78 may decrease in the proximal direction, as illustrated, for example, in FIG. 3B.

In some embodiments, the transition surface 76 and the distal surface 74 may meet at a sharp edge 82, which may reduce slipping and movement of the annular valve 34. In some embodiments, the stepped surface 70 and/or the cavity 78 may be semi-annular or arc-shaped, which may facilitate ejection during de-molding. In some embodiments, the stepped surface 70 and/or the cavity 78 may be semi-circular.

In some embodiments, the transition surface 76 may include a shoulder or an undercut. In some embodiments, the transition surface 76 may be disposed at about 90 degrees with respect to a longitudinal axis 83 of the catheter assembly 68, which may facilitate creation of the cavity 78. In some embodiments, the transition surface 76 may be disposed at an angle other than 90 degrees with respect to the longitudinal axis of the catheter assembly 10. In some embodiments, the transition surface 76 may be smooth and/or planar. In some embodiments, the transition surface 76 may be uneven, rough, or irregular. In some embodiments, the first transition surface 36 may be curved.

In some embodiments, infusion of the fluid 84 may include flushing the catheter system 18 or injecting the bolus by activating the infusion device 60 (see, for example, FIG. 2D). In some embodiments, in response to activating the infusion device 60, the annular valve 34 may be opened to allow fluid to flow from the side port 32 into the lumen 30, as illustrated, for example, in FIG. 3C.

Figure 3A:
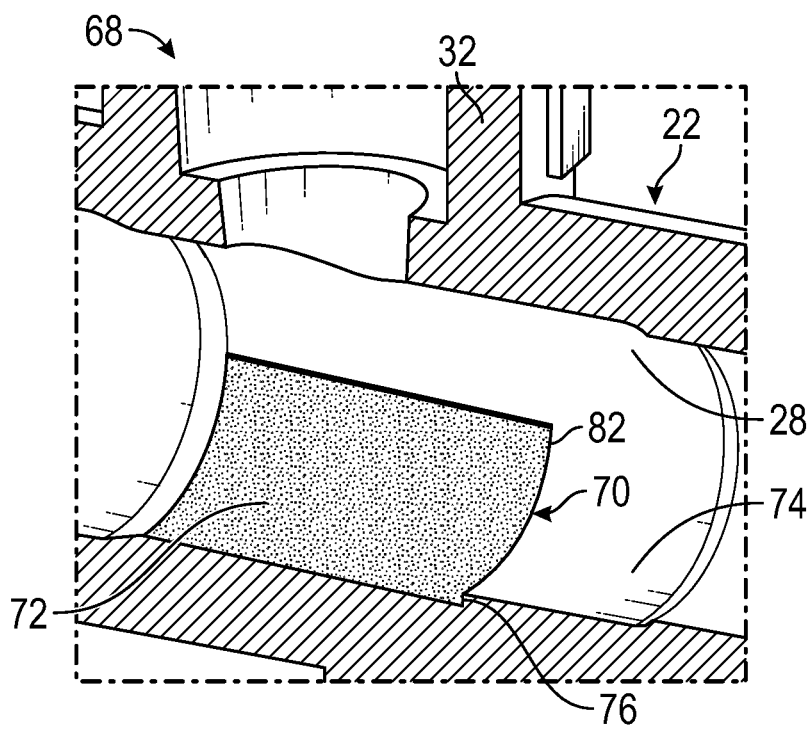
FIG. 3A is a cross-sectional view of a catheter system, illustrating an example annular valve removed for illustrative purposes, according to some embodiments.
Figure 3B:
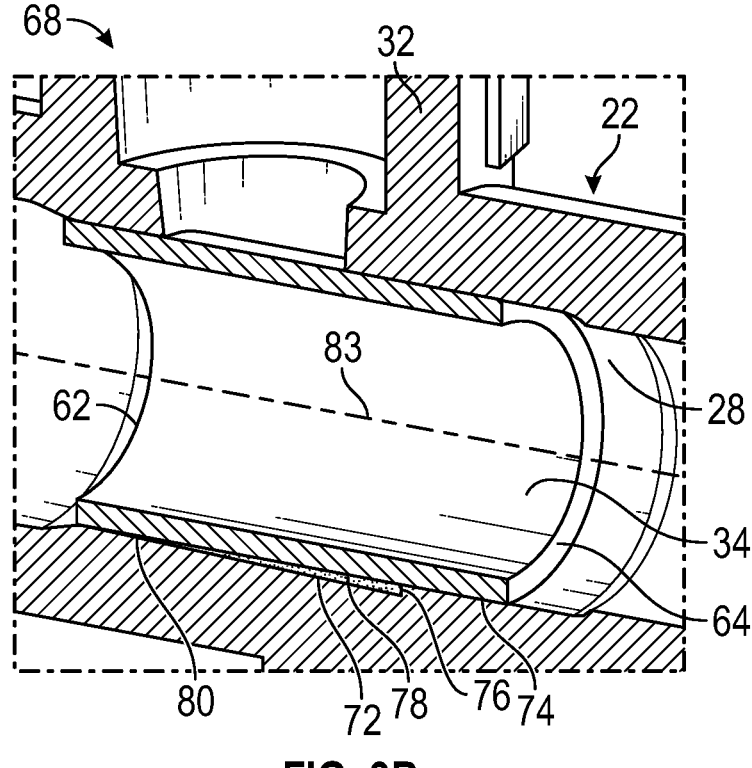
FIG. 3B is a cross-sectional view of the catheter system of FIG. 3A, illustrating the annular valve prior to fluid infusion through the side port, according to some embodiments.
Figure 3C:
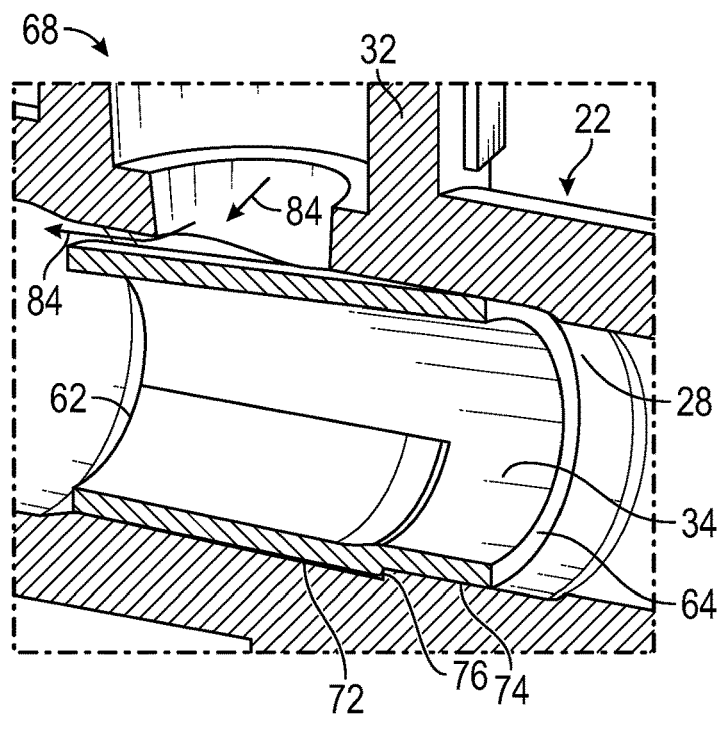
FIG. 3C is a cross-sectional view of the catheter system of FIG. 3A, illustrating the annular valve opened in response to fluid infusion, according to some embodiments.
Figure 3D:
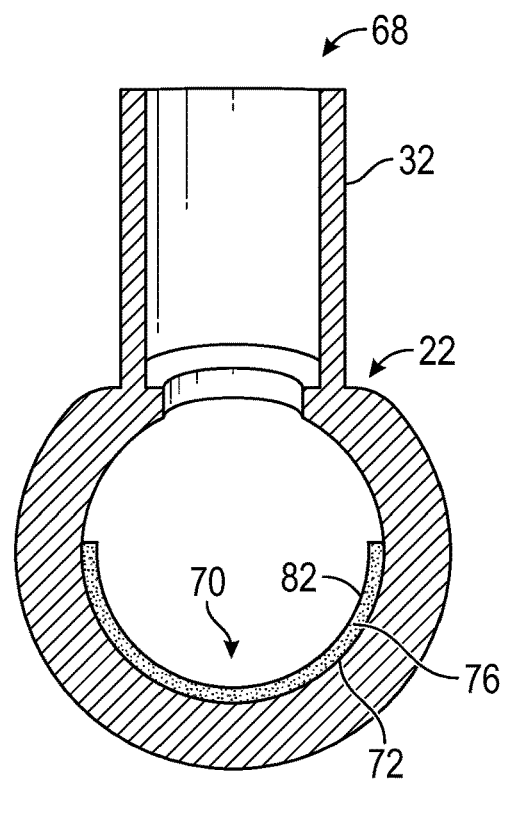
FIG. 3D is a transverse cross-sectional view of the catheter system of FIG. 3A cut proximal to an example transition surface and the annular valve removed for illustrative purposes, according to some embodiments.

In some embodiments, in response to infusion of fluid 84 through the side port 32, the annular valve 34 may decrease a size or volume of the cavity 78, as illustrated, for example, in FIG. 3C. In these embodiments, the annular valve 34 may be forced against the proximal surface 72. In some embodiments, in response to infusion of fluid 84 through the side port 32, the annular valve 34 may conform and clinch to the sharp edge 82 reducing slip of the annular valve 34. In some embodiments, the stepped surface 70 and the sharp edge 82 may reduce movement of the annular valve 34 in the distal direction and/or the proximal direction, such that the annular valve 34 continues to seal the side port 32 after the infusion of fluid 84 is complete.

In some embodiments, the cavity 78 may be empty and not include fluid prior to infusion of the fluid 84 through the side port 32. In some embodiments, in response to infusion of fluid 84 through the side port 32, the annular valve 34 may be forced against the proximal surface 72 and may not allow fluid to enter the cavity 78 during infusion of the fluid 84, such that the cavity 78 is a dead space.

In some embodiments, the transition surface 76 may be disposed towards the distal end 64 and/or the transition surface 76 may be disposed distal to an opening of the side port 32 proximate the lumen 30 and the inner surface 28, which may facilitate securement of the annular valve 34 and opening or depression of the proximal end 62 in response to infusion of fluid 84 through the side port 32. As illustrated, for example, in FIG. 3A, in some embodiments, at least the proximal surface 72 of the stepped surface 70 may include a rough surface, which may include sand blasting or chemical etching. In some embodiments, the rough surface is speckled in the drawings for illustration purposes. In some embodiments, the rough surface may increase friction between the annular valve 34 and the proximal surface 72 to decrease movement of the annular valve 34.

Figure 3E:
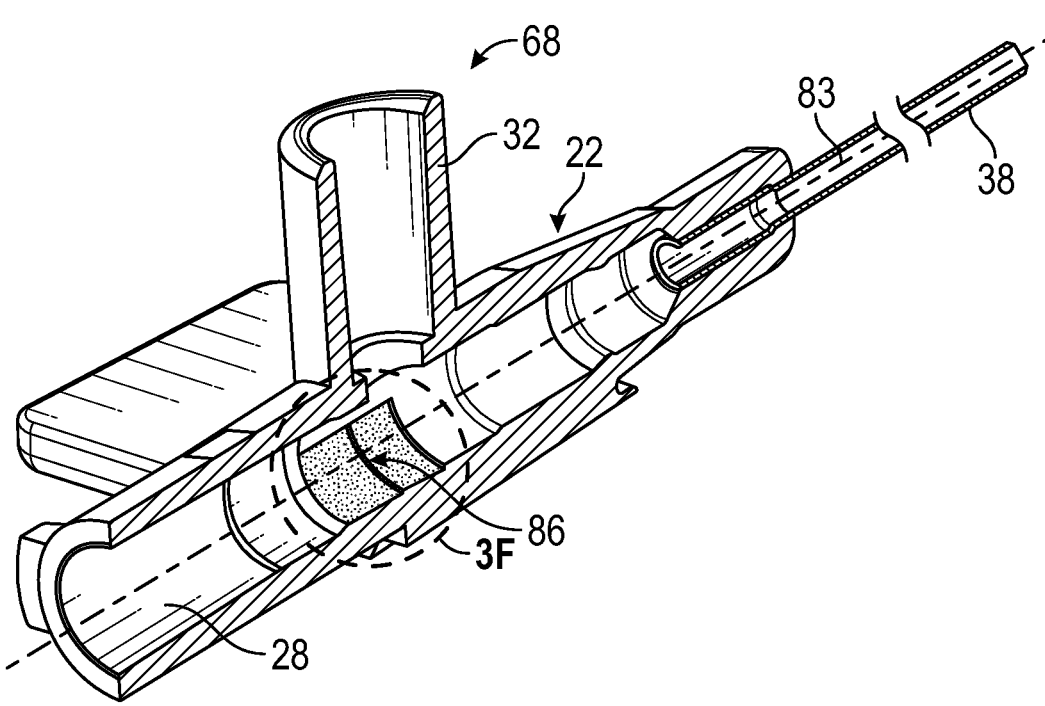
FIG. 3E is a cross-sectional view of the catheter system of FIG. 3A, illustrating two example stepped surfaces and the annular valve removed for illustrative purposes, according to some embodiments.
Figure 3F:
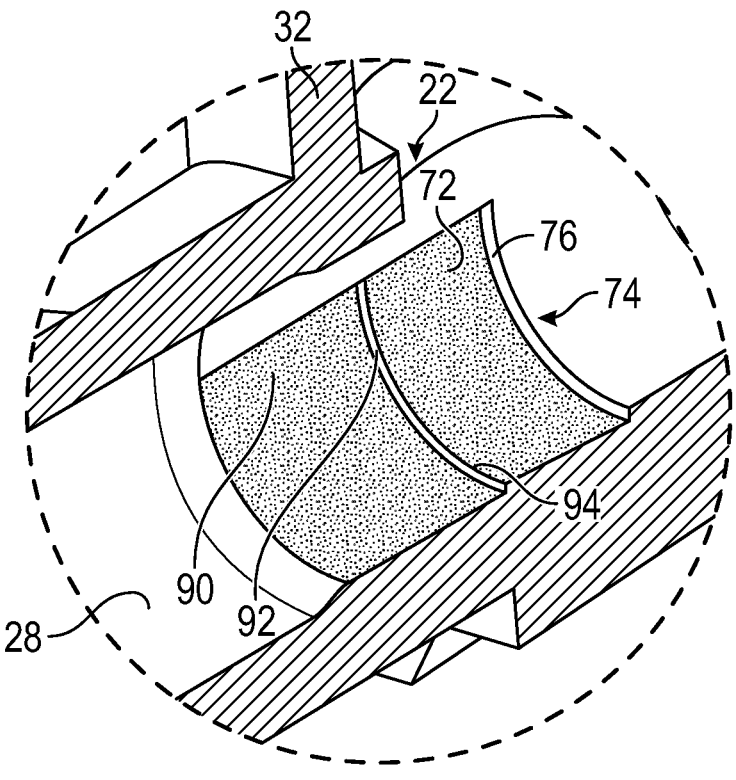
FIG. 3F is an enlarged cross-sectional view of the catheter system of FIG. 3A, illustrating the two example stepped surfaces and the annular valve removed for illustrative purposes.
Figure 3G:
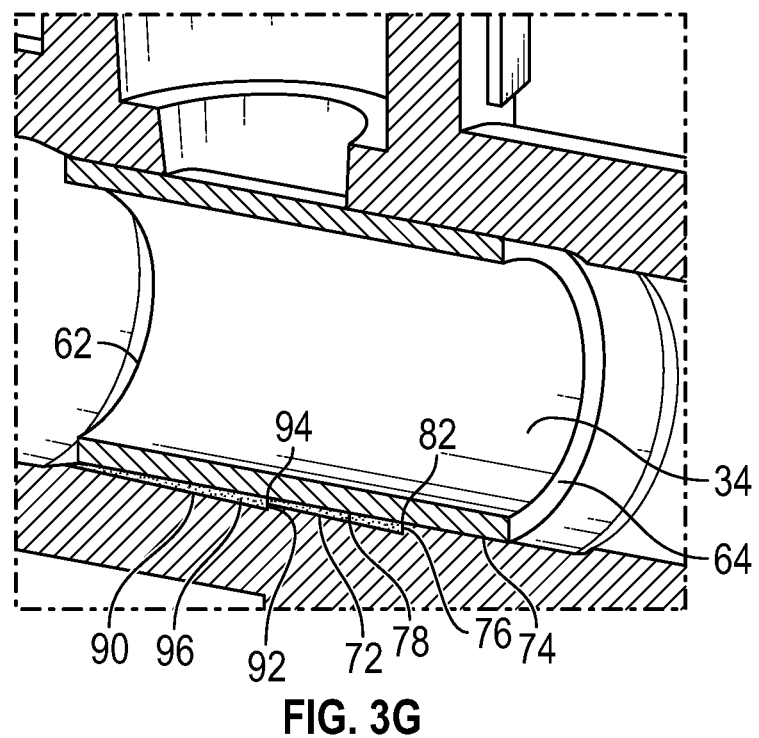
FIG. 3G is a cross-sectional view of the catheter system of FIG. 3A, illustrating the two stepped surfaces prior to fluid infusion through the side port, according to some embodiments.
Figure 3H:
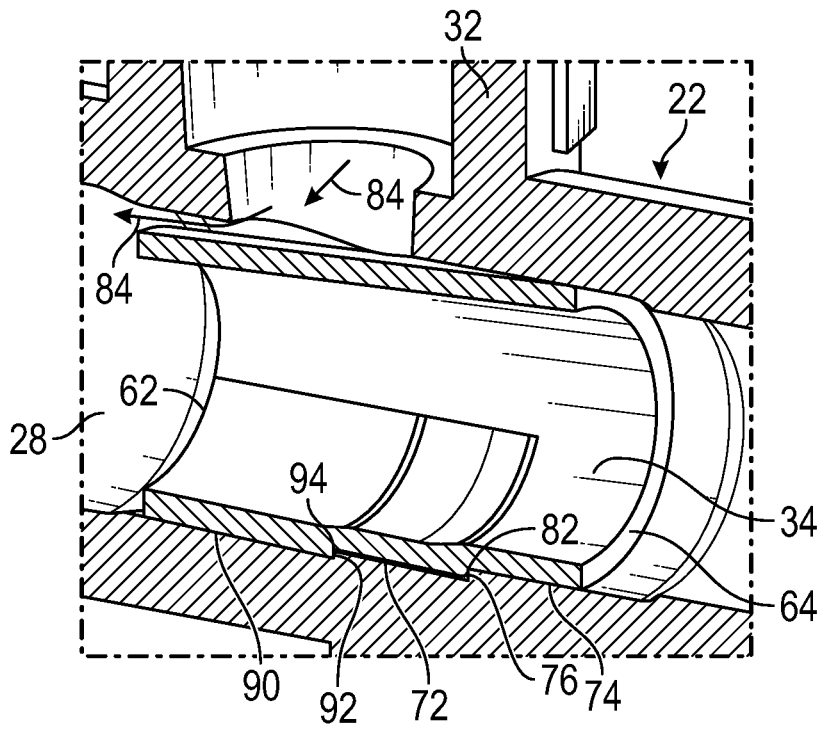
FIG. 3H is a cross-sectional view of the catheter system of FIG. 3A, illustrating the two stepped surfaces and the annular valve opened in response to fluid infusion, according to some embodiments.

Referring now to FIGS. 3E-3H, in some embodiments, the stepped surface 70 may correspond to a first stepped surface. In some embodiments, the inner surface 28 of the catheter adapter 22 may include a second stepped surface 86 proximal to the first stepped surface. In some embodiments, the second stepped surface 86 may include a distal surface that may correspond to the proximal surface 72 of the stepped surface 70. In some embodiments, the second stepped surface 86 may include a proximal surface 90 and a transition surface 92 disposed between the proximal surface 72 and the distal surface 74. In some embodiments, the second stepped surface 86 may be similar or identical to the stepped surface 70 in terms of one or more features and/or operation. As illustrated in FIGS. 3E-3F compared to FIGS. 3G-3H, in some embodiments, a location of the first stepped surface and/or the second stepped surface 86 may vary along the inner surface 28.

In some embodiments, the transition surface 92 and the distal surface of the second stepped surface 86 may meet at a sharp edge 94, which may reduce slipping and movement of the annular valve 34. In some embodiments, a cavity 96 may be disposed between an outer surface of the annular valve 34. In some embodiments, the transition surface 92 of the second stepped surface 86 may form a distal end of the other cavity 94. In these embodiments, the sharp edge 94 may contact the annular valve 34. In some embodiments, the sharp edge 94 may not contact the annular valve 34 prior to infusion, and a single semi-annular cavity may extend between the outer surface of the annular valve 34 and the inner surface 28.

In some embodiments, the second stepped surface 86 and/or the cavity 96 may be semi-annular. In some embodiments, the second stepped surface 86 and/or the cavity 78 may be semi-circular. In some embodiments, in response to infusion of fluid 84 through the side port 32, the annular valve 34 may decrease a size or volume of the cavity 96. In these embodiments, the annular valve 34 may be forced against the proximal surface 90 and the proximal surface 72. In some embodiments, in response to infusion of fluid 84 through the side port 32, the annular valve 34 may conform and clinch to the sharp edge 94 in addition to the sharp edge 82 reducing slip of the annular valve 34.

In some embodiments, the cavity 96 may be empty and not include fluid prior to infusion of the fluid 84 through the side port 32. In some embodiments, in response to infusion of fluid 84 through the side port 32, the annular valve 34 may be forced against the proximal surface 90 and may not allow fluid to enter the cavity 96 during infusion of the fluid 84, such that the cavity 96 is a dead space.

Figure 3I:
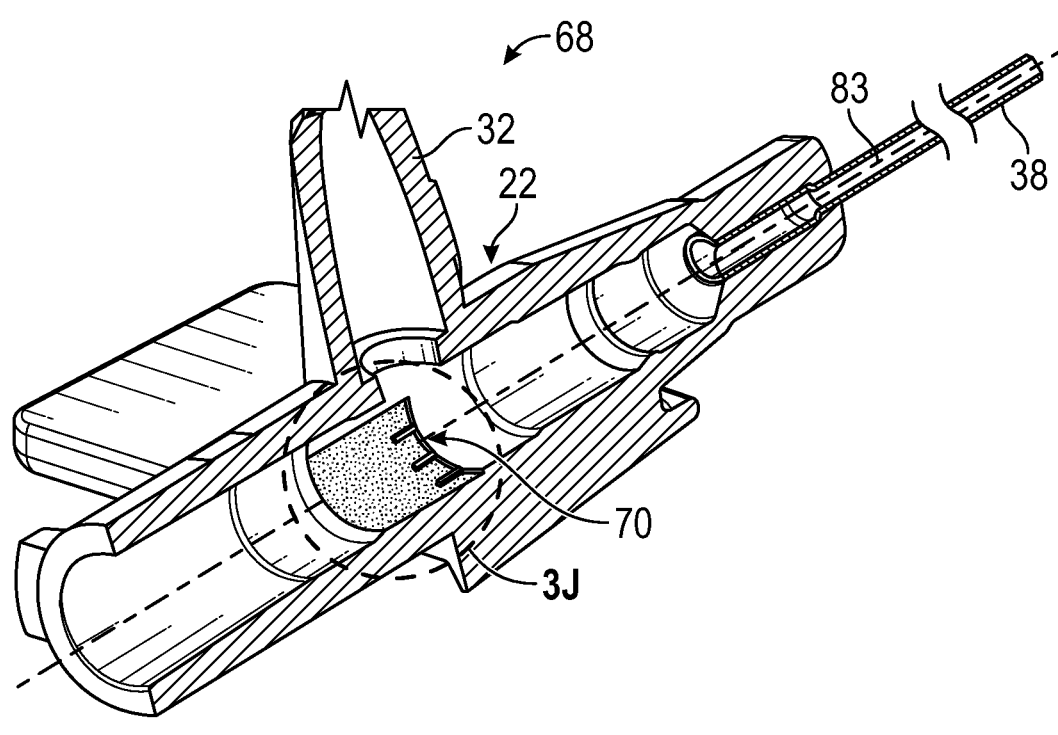
FIG. 3I is a cross-sectional view of the catheter system of FIG. 3A, illustrating multiple example ribs, according to some embodiments.
Figure 3J:
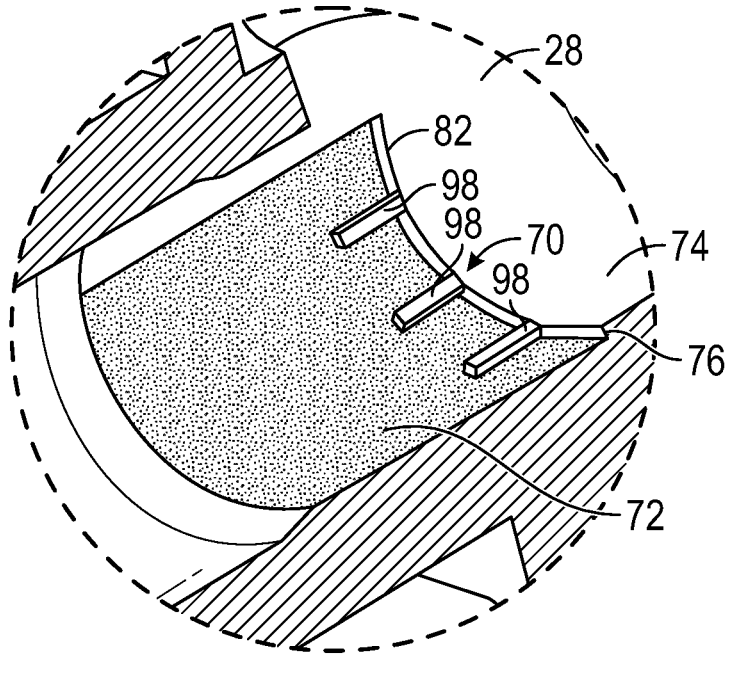
FIG. 3J is an enlarged cross-sectional view of the catheter system of FIG. 3A, illustrating the multiple example ribs, according to some embodiments.

Referring now to FIGS. 3I-3J, in some embodiments, the catheter assembly 68 may include multiple ribs 98 extending distally from a particular transition surface, such as the transition surface 76 and/or the second transition surface 92. In some embodiments, the ribs 98 may be radial and/or spaced along the particular transition surface. In some embodiments, the ribs 98 may be evenly spaced along the particular transition surface. In some embodiments, the ribs 98 may extend along a portion of a length of the proximal surface 72. In some embodiments, the ribs 98 may extend along less than half of an entire length of the proximal surface 72. In some embodiments, the ribs 98 may be aligned with the longitudinal axis 83 and/or in a direction of de-molding.

Figure 3K:
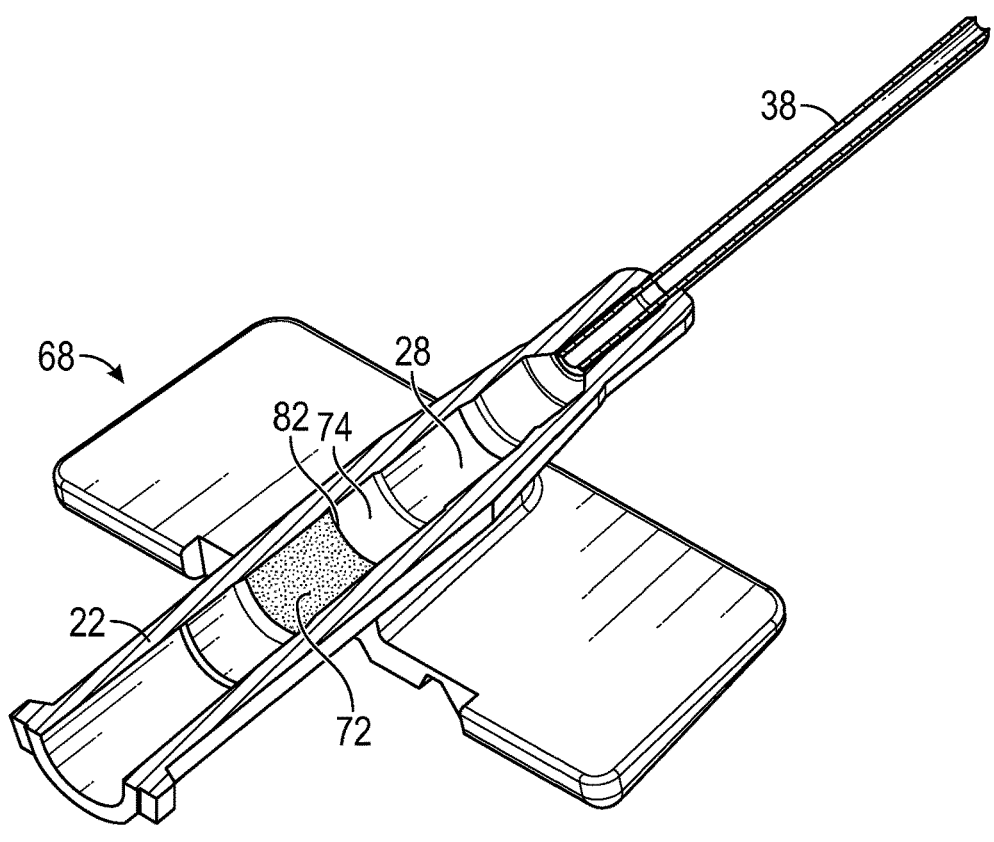
FIG. 3K is another cross-sectional view of the catheter system of FIG. 3A, according to some embodiments.

Referring now to FIG. 3K, the proximal surface 72 is illustrated from an upper perspective, according to some embodiments. In some embodiments, the proximal surface 72 and/or the distal surface 74 may be partial cylindrical surfaces. In some embodiments, the proximal surface 72 and not the distal surface 74 may include the rough surface, which may facilitate insertion of the annular valve 34 during manufacture and securement of the annular valve 34 during infusion through the side port 16. In some embodiments, the proximal surface 72 and the distal surface 74 may include the rough surface, which may facilitate securement of the annular valve 34 during infusion through the side port 16.

Figure 4A:
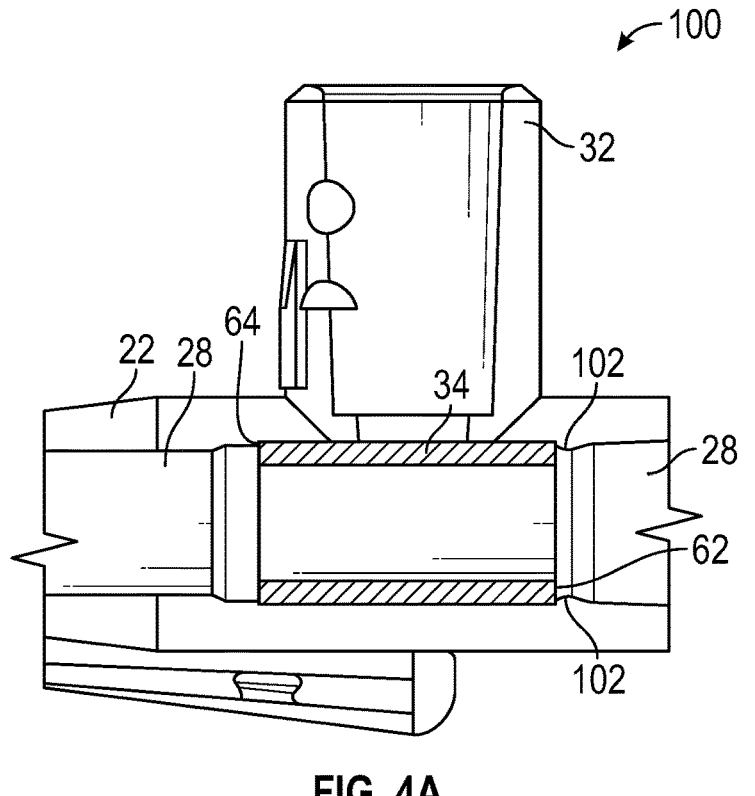
FIG. 4A is a cross-sectional view of a catheter system, illustrating multiple example bumps, according to some embodiments.
Figure 4B:
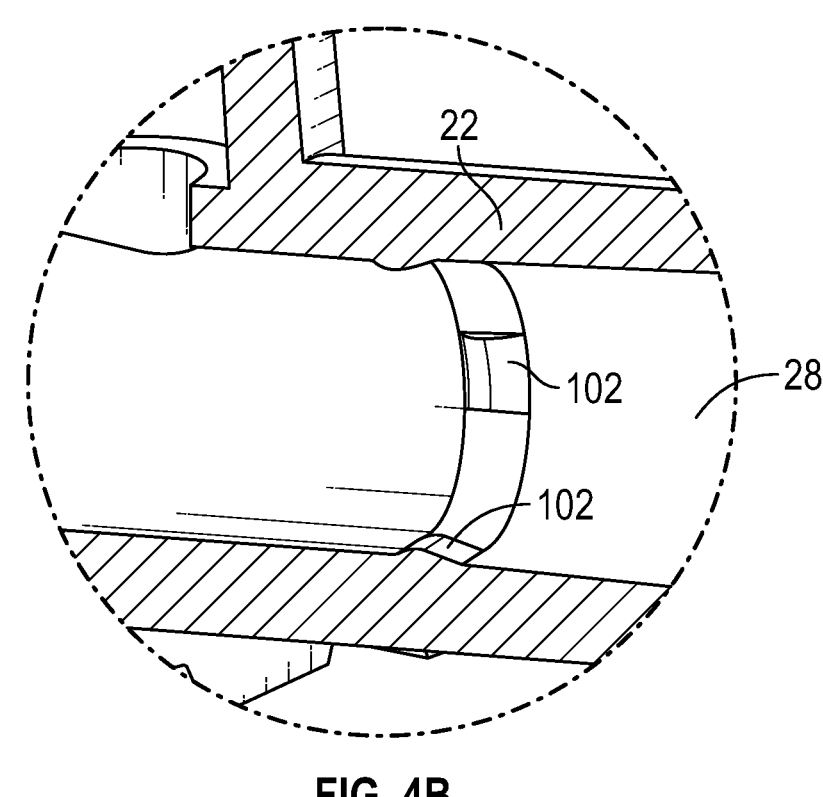
FIG. 4B is a cross-sectional view of the catheter system of FIG. 4A, illustrating the multiple bumps, and the annular valve removed for illustrative purposes, according to some embodiments.
Figure 4C:
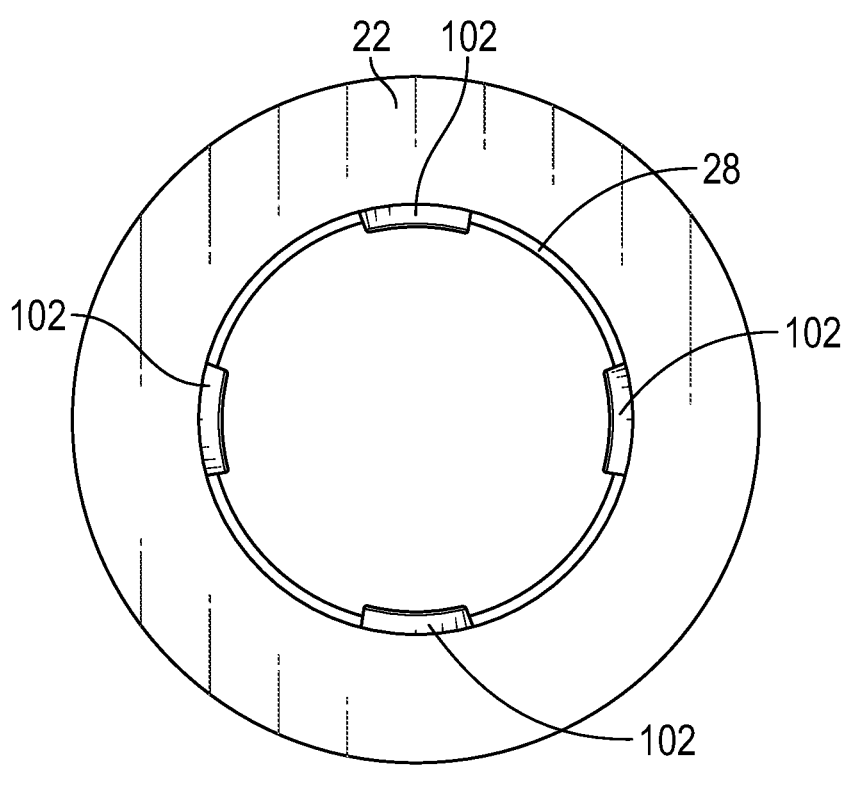
FIG. 4C is a transverse cross-sectional view of the catheter system of FIG. 4A cut immediately distal to the multiple bumps, according to some embodiments.

Referring now to FIGS. 4A-4C, a catheter assembly 100 is illustrated, according to some embodiments. In some embodiments, the catheter assembly 100 may be similar or identical to the catheter assembly 20 described with respect to FIG. 2 and/or the catheter assembly 68 described with respect to FIG. 3 in terms of one or more features and/or operation. In some embodiments, the inner surface 28 of the catheter adapter 22 may include one or more bumps 102, which may be disposed in a ring around a circumference of the inner surface 28. In some embodiments, the inner surface 28 may include four of the bumps 102 or three of the bumps 102. In some embodiments, the inner surface 28 may include more than four of the bumps 102. In some embodiments, the bumps 102 may include lengths, heights, and/or angles that are different from each other, which may increase securement of the annular valve 32 in response to infusion through the side port 16. In some embodiments, the bumps 102 may include same lengths, heights and/or angles as each other. In some embodiments, the inner surface 28 may include no more than one of the bumps 102, which may include an annular ring.

In some embodiments, the bumps 102 may be disposed proximal and/or proximate the annular valve 34 within the lumen 30. In some embodiments, the bumps 102 may be contacting the annular valve 34. In some embodiments, the bumps 102 may be rigid or semi-rigid. In some embodiments, a durometer of the bumps 102 may be greater than a durometer of the annular valve 34. In some embodiments, the bumps 102 may be monolithically formed with the inner surface 28 as a single unit.

In some embodiments, the bumps 102 may be configured to keep the annular valve 34 in a same or similar position in response to fluid infusion through the side port 32 that opens the annular valve 34. In further detail, in some embodiments, the bumps 102 may be configured to reduce proximal movement of the annular valve 34 in response to fluid infusion through the side port 32 that opens the annular valve 34. In some embodiments, in response to fluid infusion through the side port 32 that opens the annular valve 34, the proximal end 62 of the annular valve 34 may not move in the proximal direction. In some embodiments, in response to fluid infusion through the side port 32 that opens the annular valve 34, movement of the annular valve 34 in the proximal direction may be reduced. Thus, in some embodiments, the bumps 102 may prevent fluid, such as blood and/or another fluid, from leaking through the annular valve 34 and out the side port 32.

Figure 5A:
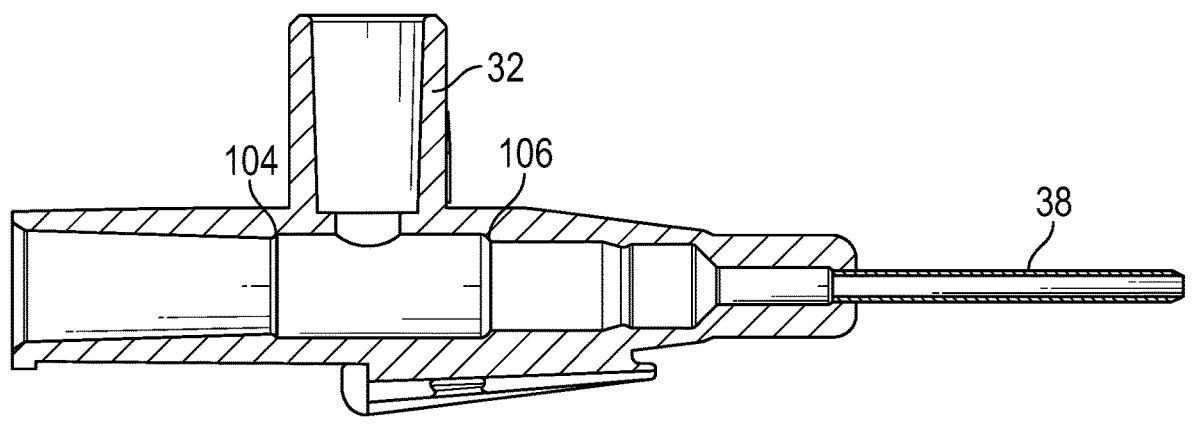
FIG. 5A is a cross-sectional view of a catheter system, illustrating an example proximal undercut and an example distal undercut and the annular valve removed for illustrative purposes, according to some embodiments.
Figure 5B:
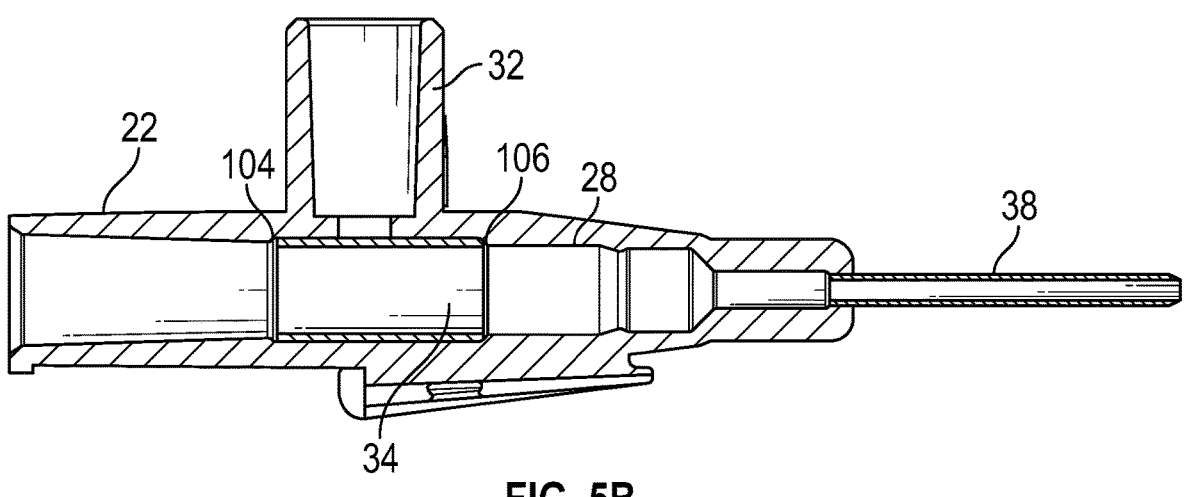
FIG. 5B is a cross-sectional view of the catheter system of FIG. 5A, according to some embodiments.

Referring now to FIGS. 5A-5B, a catheter assembly 103 is illustrated, according to some embodiments. In some embodiments, the catheter assembly may be similar or identical to one or more of the following in terms of one or more features and/or operation: the catheter assembly 20 described with respect to FIG. 2, the catheter assembly 68 described with respect to FIG. 3, and the catheter assembly 100 described with respect to FIG. 4.

In some embodiments, the inner surface 28 may include a proximal undercut 104 and a distal undercut 106, and the annular valve 34 may be disposed between the proximal undercut 104 and the distal undercut 106. In some embodiments, the proximal undercut 104 and/or the distal undercut 106 may be annular. In some embodiments, a length of the annular valve 34 may be approximately equal to a distance between the proximal undercut 104 and the distal undercut 106 such that the annular valve 34 abuts the proximal undercut 104 and the distal undercut 106. In some embodiments, the distal edge 48 and the proximal edge 50 may be annular. In some embodiments, the annular valve 34 may fit snugly within the proximal undercut 104 and the distal undercut 106. In some embodiments, the proximal undercut 104 and the distal undercut 106 may form a cavity in which the annular valve 34 may be seated.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
a catheter assembly, comprising:
a catheter adapter, comprising a distal end, a proximal end, an inner surface forming a lumen extending through the distal end and the proximal end, and a side port disposed between the distal end and the proximal end, wherein the inner surface of the catheter adapter comprises a stepped surface positioned opposite the side port, wherein the stepped surface comprises a distal surface, a proximal surface, and a transition surface disposed between the distal surface and the proximal surface, the transition surface being positioned distal to the side port, the transition surface facing in a proximal direction;
an annular valve disposed within the lumen, wherein the annular valve seals a fluid pathway from the side port to the lumen, wherein the annular valve includes a proximal portion that extends along and contacts the proximal surface and a distal portion that extends along and contacts the distal surface such that a cavity is formed between an outer surface of the annular valve and the proximal surface, the cavity extending distally to the transition surface, wherein the proximal surface has a rough texture and the distal surface has a smooth texture, wherein the proximal portion of the annular valve is configured to deflect when fluid is injected through the side port to form a fluid pathway from the side port and into the proximal end of the catheter adapter, and wherein the deflection caused when the fluid is injected also causes the annular valve to be forced distally into the cavity and against the transition surface such that the transition surface prevents the annular valve from sliding distally within the lumen; and a catheter extending distally from the distal end of the catheter adapter.

2. The catheter system of claim 1, wherein a depth of the cavity decreases in a proximal direction.

3. The catheter system of claim 1, wherein the transition surface and the distal surface meet at a sharp edge.

4. The catheter system of claim 1, wherein the stepped surface and the cavity are semi-annular.

5. The catheter system of claim 1, wherein the proximal surface comprises sand blasting or chemical etching.

6. The catheter system of claim 1, wherein the stepped surface is a first stepped surface, wherein the inner surface of the catheter adapter further comprises a second stepped surface proximal to the first stepped surface, further comprising another cavity disposed between the outer surface of the annular valve, wherein another transition surface of the second stepped surface forms a distal end of the another cavity.

7. A catheter system, comprising:

a catheter assembly, comprising:

a catheter adapter, comprising a distal end, a proximal end, an inner surface forming a lumen, the lumen extending through the distal end and the proximal end, and a side port disposed between the distal end and the proximal end;

an annular valve disposed within the lumen and aligned with the side port, wherein the annular valve seals a fluid pathway from the side port to the lumen, wherein the annular valve includes a proximal portion that extends along and contacts a proximal surface and a distal portion that extends along and contacts a distal surface, wherein the proximal surface has a rough texture and the distal surface has a smooth texture, the annular valve having the proximal portion that extends proximally beyond the side port and the distal portion that extends distally beyond the side port, wherein the proximal portion of the annular valve is configured to deflect when fluid is injected through the side port to form a fluid pathway from the side port and into the proximal end of the catheter adapter;

a retainer ring disposed proximal to and in contact with the annular valve within the lumen, wherein the proximal portion of the annular valve deflects relative to the retainer ring such that the fluid pathway is formed through the retainer ring; and a catheter extending distally from the distal end of the catheter adapter.

8. The catheter system of claim 7, wherein the inner surface comprises an undercut, wherein the retainer ring is disposed within the undercut.

9. The catheter system of claim 7, wherein the inner surface comprises a proximal undercut and a distal undercut, wherein the annular valve is disposed between the proximal undercut and the distal undercut.

10. The catheter system of claim 7, wherein the annular valve is cylindrical.

11. The catheter system of claim 7, wherein the retainer ring is rigid.

12. The catheter system of claim 7, wherein the retainer ring is plastic and the annular valve is silicone.

13. The catheter system of claim 7, further comprising a needle assembly, wherein the needle assembly comprises a needle hub and an introducer needle extending distally from the needle hub and through the retainer ring, the annular valve, and the catheter.

14. A catheter system, comprising:

a catheter assembly, comprising:

a catheter adapter, comprising a distal end, a proximal end, an inner surface forming a lumen extending through the distal end and the proximal end, and a side port disposed between the distal end and the proximal end, wherein the inner surface of the catheter adapter comprises a stepped surface positioned opposite the side port, wherein the stepped surface comprises a distal surface, a proximal surface, and a transition surface disposed between the distal surface and the proximal surface, the transition surface being positioned distal to the side port, the transition surface facing in a proximal direction, wherein the proximal surface has a rough texture and the distal surface has a smooth texture;

an annular valve disposed within the lumen, the annular valve being formed of silicone, wherein the annular valve seals a fluid pathway from the side port to the lumen, wherein the annular valve includes a proximal portion that extends along and contacts the proximal surface and a distal portion that extends along and contacts the distal surface such that a cavity is formed between the outer surface of the annular valve and the proximal surface, the cavity extending distally to the transition surface, wherein the proximal portion of the annular valve is configured to deflect when fluid is injected through the side port to form a fluid pathway from the side port and into the proximal end of the catheter adapter, and wherein the deflection caused when the fluid is injected also causes the annular valve to be forced distally into the cavity and against the transition surface such that the transition surface prevents the annular valve from sliding distally within the lumen; and a catheter extending distally from the distal end of the catheter adapter.

* * * * *